United States Patent
Charles

(10) Patent No.: US 12,274,522 B2
(45) Date of Patent: Apr. 15, 2025

(54) DIRECT DRIVE ROBOT FOR VITREORETINAL SURGERY

(71) Applicant: Alcon Inc., Fribourg (CH)

(72) Inventor: Steven T. Charles, Memphis, TN (US)

(73) Assignee: Alcon Inc., Fribourg (CH)

( * ) Notice: Subject to any disclaimer, the term of this patent is extended or adjusted under 35 U.S.C. 154(b) by 417 days.

(21) Appl. No.: 17/649,569

(22) Filed: Feb. 1, 2022

(65) Prior Publication Data

US 2022/0249183 A1 Aug. 11, 2022

Related U.S. Application Data

(60) Provisional application No. 63/146,137, filed on Feb. 5, 2021.

(51) Int. Cl.
*A61B 34/00* (2016.01)
*A61B 34/20* (2016.01)
(Continued)

(52) U.S. Cl.
CPC .............. *A61B 34/37* (2016.02); *A61B 34/20* (2016.02); *A61B 34/25* (2016.02); *A61B 34/76* (2016.02);
(Continued)

(58) Field of Classification Search
CPC ........ A61B 2034/306; A61B 2034/305; A61B 2034/304; A61B 2034/303; A61B 2034/302; A61B 2034/301; A61B 34/37; A61B 34/35; A61B 34/32; A61B 34/30; A61B 34/72; A61B 90/37; A61B 34/76;
(Continued)

(56) References Cited

U.S. PATENT DOCUMENTS 6,330,837 B1 * 12/2001 Charles ................ B25J 17/0266
901/29
6,516,681 B1 * 2/2003 Pierrot ................... B25J 9/0051
901/23
(Continued)

FOREIGN PATENT DOCUMENTS

RU 2491161 C1 8/2013
WO WO2020256503 A2 * 12/2020 ............. A61B 34/37

*Primary Examiner* — Shaun L David
*Assistant Examiner* — Mitchell Brian Hoag

(57) ABSTRACT

The present disclosure relates to high dexterity robotic manipulation systems for ophthalmic microsurgical procedures. In certain embodiments, a robotic surgical system includes a master apparatus controllably coupled to a slave apparatus. The slave apparatus mounts to a patient's head and includes a dual tripod structure having two pluralities of linear actuator links pivotally supporting a surgical tool. The motions of the actuator links are controlled by direct drive actuators to provide at least 6-DOF for the surgical tool. A passive articulating arm having a SCARA mechanism and four-bar parallelogram mechanism attaches to the slave apparatus and counterbalances the weight thereof when mounted on a patient. The surgical system also includes sensors communicatively coupled to the slave apparatus and master apparatus to enable force feedback and force control. Accordingly, the robotic surgical system enhances the dexterity of an operator and enables performance of medical procedures more easily than by hand.

12 Claims, 9 Drawing Sheets

(51) Int. Cl.
  *A61B 34/37* (2016.01)
  *A61B 90/00* (2016.01)
  *A61B 34/30* (2016.01)
  *A61F 9/007* (2006.01)

(52) U.S. Cl.
  CPC ........ *A61B 90/37* (2016.02); *A61B 2034/304* (2016.02); *A61B 34/72* (2016.02); *A61B 34/75* (2016.02); *A61B 34/77* (2016.02); *A61F 9/007* (2013.01); *A61F 9/00736* (2013.01)

(58) Field of Classification Search
  CPC .... A61B 34/20; A61B 2090/502; A61B 90/50
  USPC .......................................................... 606/130
  See application file for complete search history.

(56) References Cited

U.S. PATENT DOCUMENTS

| | | | | |
|---|---|---|---|---|
| 8,272,290 | B2* | 9/2012 | Zhang | B25J 9/107 74/490.03 |
| 8,714,903 | B2* | 5/2014 | Feng | B25J 15/0616 414/735 |
| 8,882,437 | B2* | 11/2014 | Nakanishi | H01L 21/6838 294/902 |
| 9,211,647 | B2* | 12/2015 | Nagayama | B25J 9/0051 |
| 10,646,990 | B2* | 5/2020 | Olds | B25J 9/0051 |
| 10,821,599 | B2* | 11/2020 | Crawford | B25J 9/0048 |
| 10,830,567 | B2* | 11/2020 | Angood | B25J 9/1623 |
| 10,941,843 | B2* | 3/2021 | Krishna | B25J 17/00 |
| 11,049,410 | B2* | 6/2021 | Talke | G09B 9/12 |
| 11,666,126 | B2* | 6/2023 | Cowley | A45B 23/00 135/20.1 |
| 2003/0005786 | A1* | 1/2003 | Stuart | B25J 17/0266 409/235 |
| 2006/0025689 | A1* | 2/2006 | Chalana | A61B 8/0883 600/456 |
| 2008/0200926 | A1* | 8/2008 | Verard | A61B 90/90 606/130 |
| 2009/0216191 | A1* | 8/2009 | Loeffel | A61B 34/76 604/131 |
| 2010/0234856 | A1* | 9/2010 | Stoianovici | A61B 34/70 606/130 |
| 2010/0275718 | A1* | 11/2010 | Stuart | B25J 17/0266 74/490.01 |
| 2010/0331858 | A1* | 12/2010 | Simaan | A61B 34/30 623/1.11 |
| 2014/0005555 | A1* | 1/2014 | Tesar | A61B 1/00193 600/476 |
| 2017/0010671 | A1* | 1/2017 | Ghaffari Toiserkan | B25J 9/1689 |
| 2017/0245954 | A1* | 8/2017 | Beira | A61B 34/37 |
| 2019/0000447 | A1* | 1/2019 | Shelton, IV | A61B 17/07292 |
| 2019/0038369 | A1* | 2/2019 | Naus | A61B 34/70 |
| 2020/0054356 | A1* | 2/2020 | Miller | A61B 17/320758 |
| 2020/0100856 | A1* | 4/2020 | Hongo | B25J 13/02 |
| 2020/0121403 | A1* | 4/2020 | Awano | B25J 9/1664 |
| 2020/0121406 | A1* | 4/2020 | Lee | A61B 17/29 |
| 2020/0129254 | A1* | 4/2020 | Kang | A61B 34/75 |
| 2020/0155249 | A1* | 5/2020 | Govari | A61B 90/06 |
| 2020/0168322 | A1* | 5/2020 | Brandt | A61B 50/24 |
| 2020/0205907 | A1* | 7/2020 | Doi | A61B 34/30 |
| 2020/0253678 | A1* | 8/2020 | Hulford | A61B 34/25 |
| 2020/0337790 | A1* | 10/2020 | Mumaw | A61B 34/71 |
| 2020/0405414 | A1* | 12/2020 | Shelton, IV | A61B 17/320092 |
| 2020/0410180 | A1* | 12/2020 | Shelton, IV | A61B 17/10 |
| 2021/0015573 | A1* | 1/2021 | Tsao | A61B 34/35 |
| 2021/0022799 | A1* | 1/2021 | Fischvogt | A61B 18/1445 |
| 2021/0145530 | A1* | 5/2021 | Martin | B25J 13/02 |
| 2021/0378756 | A1* | 12/2021 | Calloway | A61B 90/361 |
| 2022/0039872 | A1* | 2/2022 | Leonard | A61B 1/00009 |

\* cited by examiner

DIRECT DRIVE ROBOT FOR VITREORETINAL SURGERY

FIELD

Embodiments of the present disclosure generally relate to robotic manipulation systems for surgical procedures, and more particularly, direct drive robotic manipulation systems for ophthalmic microsurgical procedures.

BACKGROUND

Retinal microsurgery, and in particular, vitreoretinal surgery, is among the most challenging ophthalmic surgical procedures. As the name implies, vitreoretinal eye surgery is performed in the gel-like vitreous and on surfaces of the light-sensitive retina within the relatively small ocular space. Common conditions necessitating vitreoretinal surgery include epimacular membranes, vitreomacular schisis, vitreomacular traction syndrome, diabetic traction retinal detachments, proliferative vitreoretinopathy (PVR), retinal detachment, and macular holes, in addition to various treatments such as microinjection procedures for gene therapy and scaffold placements for cell based therapies.

During vitreoretinal surgery, surgeons must perform precise micron-scale maneuvers while applying diminutive forces to retinal tissues beyond the natural human levels of sensory perception. Thus, performance of vitreoretinal surgery is inherently restricted by human sensory and motor limitations, surgeon fatigue and hand tremor, imprecise instrumentation, fine feature sizes, limited manipulation room within the ocular space, and occasionally poor visualization of the interior of the eye. In addition to the above limitations, serious complications may also be caused by involuntary patient eye and/or head movement. The aforementioned factors may contribute to a variety of surgical complications including retinal breaks, retinal detachment, hemorrhage, damage to retinal blood vessels, and damage to the lens resulting in cataracts, many of which can develop into potentially irreversible damage and visual impairment.

Recently, robotically-assisted surgical devices have been developed to assist surgeons in the performance of minimally invasive ophthalmic surgeries, including vitreoretinal surgery. Yet, these robotic devices still suffer from several drawbacks, including the high risk of complications from patient eye movement during surgery. To minimize this risk, digital eye tracking has been proposed for use by these robotic devices. However, current eye tracking technologies are not advanced enough to detect and correct for sudden head and eye movements, which may be caused by sleep apnea or a startled response upon awakening from sedation.

Furthermore, most current robotic ophthalmic surgical systems do not provide force control (e.g., scaling, limiting, filtering) or force feedback (e.g., tactile feedback) while maintaining a high degree of freedom of movement, and instead typically only provide some form of scaling, thus not effectively addressing the sensory and motor limitations of surgeons. Additional limitations associated with current robotically-assisted surgical devices and systems include limited flexibility and serial kinematics. Current robotic systems are characterized by 4 degrees-of-freedom (4-DOF), which is insufficient to address patient head and/or eye movement or rotate the eye to visualize around corneal or lens opacities, as well as visualize the peripheral retina during ophthalmic procedures. Further, serial robots, such as articulated robotic arms, are disadvantaged by cumulative joint error, kinematic singularities, decreased precision, and decreased speed. Thus, current robotically-assisted surgical devices and systems lack the dexterity to precisely and effectively execute the micron-scale maneuvers regularly performed during vitreoretinal surgery and respond to sudden heady and eye movement of the patient.

Accordingly, there is a need in the art for robotic surgical systems with improved dexterity and accuracy for ophthalmic microsurgical procedures.

SUMMARY

The present disclosure relates to robotic manipulation systems for surgical procedures, and more particularly, to high dexterity direct drive robotic systems for ophthalmic microsurgical procedures.

In certain embodiments, a surgical system is provided, including a master apparatus and a slave apparatus controllably coupled to the master apparatus and further configured to be mounted to a patient's head. The slave apparatus includes a support frame coupled to a first and second set of three linearly-actuating links, wherein each link of a set is spaced apart from an adjacent link by an angle less than or equal to about 120 degrees. The slave apparatus further includes a surgical tool pivotally supported by each of the links, which are configured to provide translational and rotational movement to the surgical tool. The surgical system also includes one or more direct drive actuators coupled to each link of the first and second sets to provide linear movement to the links.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end or portion of a component refers to the end or the portion that is closer to a patient's body during use thereof. On the other hand, a proximal end or portion of the component refers to the end or the portion that is distanced further away from the patient's body.

As used herein, the term "about" may refer to a +/−10% variation from the nominal value. It is to be understood that such a variation can be included in any value provided herein.

Embodiments of the present disclosure generally relate to robotic surgical systems for surgical procedures, and more particularly, to high dexterity direct drive robotic systems for ophthalmic microsurgical procedures. In certain embodiments, a robotic surgical system includes a master apparatus controllably coupled to a slave apparatus. The slave apparatus mounts to a patient's head and includes a dual tripod structure having two pluralities of linear actuator links pivotally supporting a surgical tool. The motions of the actuator links are controlled by direct drive actuators to provide at least 6-DOF for the surgical tool. A passive articulating arm having a SCARA (Selectively Compliant Articulated Robot Arm) mechanism and a four-bar parallelogram mechanism attaches to the slave apparatus and counterbalances the weight thereof when mounted on a patient. The surgical system also includes sensors communicatively coupled to the slave apparatus and master apparatus to enable force feedback and force control. Accordingly, the robotic surgical system enhances the dexterity of an operator and enables performance of medical procedures more easily than by hand.

Figure 1:
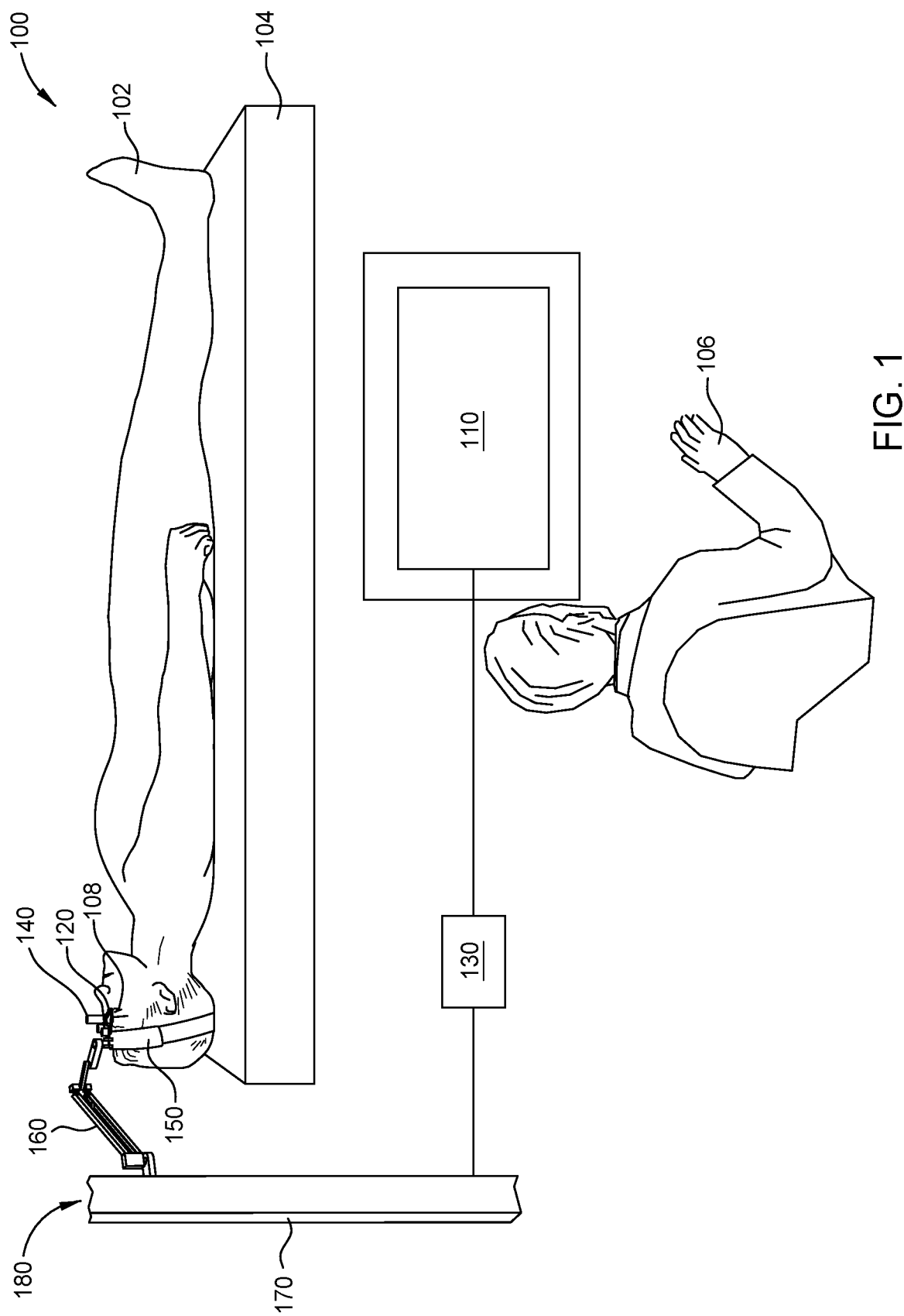
FIG. 1 illustrates a schematic view of an exemplary robotic surgical system, according to certain embodiments of the present disclosure.

FIG. 1 illustrates a schematic view of an exemplary robotic surgical system 100, according to certain embodiments described herein. The robotic surgical system 100 employs a master-slave type robotic system that includes a master apparatus 110 and a slave apparatus 120. The master apparatus 110 may be any suitable type of master device characterized by six degrees of freedom (6-DOF) or seven degrees of freedom (7-DOF) that has an operator interface. In certain embodiments, the master apparatus 110 includes a 6-DOF or 7-DOF haptic interface with low inertia and friction. One such example of a suitable master device with a haptic interface is the Freedom6S haptic device available from MPB Technologies, Inc.

In certain embodiments, the master apparatus 110 includes a haptic interface modeled to match (e.g., resemble) the slave apparatus 120. For example, the master apparatus 110 may have a structure substantially similar to that of the slave apparatus 120, described in greater detail below. When an operator 106 operates the master apparatus 110, the master apparatus 110 generates a plurality of signals, herein collectively referred to as a "control signal," that is transmitted between the master apparatus 110, a programmed computer 130, and the slave apparatus 120. Receiving the control signal, the slave apparatus 120 controls the manipulation and/or operation of a surgical tool 140 directly or indirectly coupled thereto to perform an ophthalmic surgical procedure.

The slave apparatus 120, and therefore the surgical tool 140, are placed over an eye 108 of a patient 102, who is shown in FIG. 1 as lying in a surgical position on an operating table 104. The slave apparatus 120 is at least partially supported over the patient's eye 108 by a slave apparatus support system 180 including a forehead support 150 configured to mount to (e.g., rest on) the patient's head. By mounting the slave apparatus 120 to the patient's head, the risks associated with uncontrolled patient head movement during a surgical procedure can be greatly reduced or eliminated. The forehead support 150 is further coupled to an articulating arm 160 employing a passive four-bar parallelogram mechanism counterbalanced by an air spring or constant force spring to alleviate pressure on the patient's head caused by the weight of the slave apparatus 120 and forehead support 150. The articulating arm 160 may be supported by a base 170, such as a support post, or may extend from another surgical device or a ceiling of an operating room. Further details regarding the slave apparatus 120, forehead support 150, and articulating arm 160 are provided below with reference to FIGS. 2A-5B.

The surgical tool 140 includes any suitable surgical device or apparatus for ophthalmic surgical procedures, such as vitreoretinal surgical procedures. For example, the surgical tool 140 may be a forceps, shaver, shear, cutter, or other non-actuated device. In certain embodiments, the surgical tool 140 is configured to perform surgical maneuvers, such as membrane peeling, segmentation, delamination of epiretinal membranes, retinal incisions, subretinal injections, or the like. In certain embodiments, the surgical tool 140 includes an end effector having one or more actuators for enabling direct manipulation of the end effector secured thereto.

In certain embodiments, the surgical tool 140 includes an end effector having a 6-DOF force/torque sensor (i.e., transducer) incorporated therein to facilitate force feedback and force control by the robotic surgical system 100. In still further embodiments, the surgical tool 140 is a device holder or sleeve configured to secure another device or tool to the slave apparatus 120, and includes a radio frequency identification (RFID) or quick response (QR) barcode sensor in communication therewith to communicate tool weight (facilitating a weightless tool), moment arms (facilitating center of gravity compensation as orientation of the surgical tool 140 changes in space), and tool length and offsets (facilitating consistent master-slave pose relationship) to the computer 130. Generally, tool actuation pneumatic or hydraulic connections, fiber optic connections, aspiration and/or injection connections, and an uninterruptible power supply connection may be incorporated into the surgical tool 140 or bypass the surgical tool 140 via service loops.

Figure 2A:
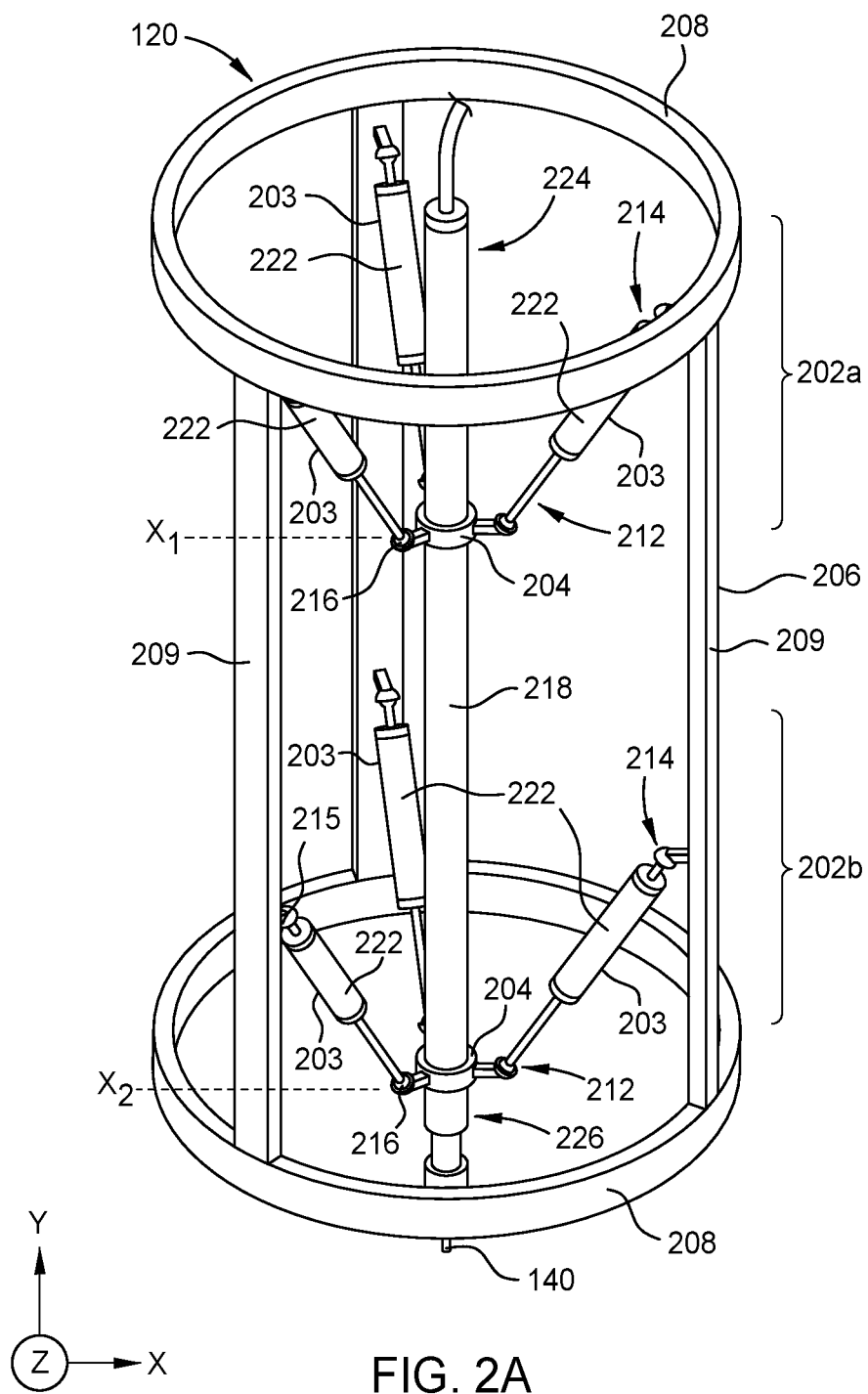
FIG. 2A illustrates an example perspective view of a slave apparatus of the robotic surgical system of FIG. 1, according to certain embodiments of the present disclosure.

FIG. 2A illustrates a perspective view of the slave apparatus 120 of the robotic surgical system 100, according to certain embodiments. The slave apparatus 120 is configured to be mounted over the patient's eye 108 and manipulate and/or operate a surgical tool 140 directly or indirectly attached thereto. In the embodiment of FIG. 2A, the surgical tool 140 is coupled to a distal end of a tool shaft 218, which, in certain embodiments, is a device holder or sleeve.

As depicted, the tool shaft 218 is movably coupled to two sets 202*a*, 202*b* of three radially-extending and linearly-actuating actuator links 203 that act as the drive train for the slave apparatus 120. Actuation of the actuator links 203 results in manipulation of the tool shaft 218 and thus, the surgical tool 140, and is determined by the control signal received from the master apparatus. The two sets of actuator links 203 include a first proximal set 202*a* and a second distal set 202*b* having parallel kinematics, thus enabling the two sets 202*a*, 202*b* to linearly move in concert (i.e., synchronously) to manipulate the tool shaft 218 and thus, the surgical tool 140, in response to control signals from the master apparatus 110. Utilization of a parallel and closed loop kinematic chain for the two sets 202*a*, 202*b* of actuator links 203 enables decreased structural weight and increased precision, stability, link rigidity, and acceleration, as compared to a single articulating arm equipped with serial kinematics. The parallel kinematic design of the slave apparatus 120 further enables differential drive of the two sets 202*a*, 202*b* of actuator links 203, thus providing greater maneuverability of the tool shaft 218 and surgical tool 140 while facilitating the averaging of joint error in the parallel link structure.

Each set 202*a*, 202*b* of actuator links 203 may be coupled to the tool shaft 218 at distal ends 212 of the actuator links 203 by a coupling ring 204 such that the actuator links 203 of each set 202*a*, 202*b* are attached to the tool shaft 218 on a single plane $X_1$ or $X_2$. The planes $X_1$ and $X_2$ are located at a proximal end 224 and a distal end 226 of the tool shaft 218, respectively. Accordingly, the embodiment of FIG. 2A may be described as a dual parallel tripod slave apparatus 120, having two sets 202*a*, 202*b* of three actuator links 203 (e.g., "three plus three") extending radially outward from the tool shaft 218 at two different horizontal planes, thus forming two tripods of actuator links 203. The actuator links 203 may be radially spaced apart from adjacent actuator links 203 of the same set 202 by an angle of about 120° relative to the tool shaft 218.

Note that although three actuator links 203 are depicted in each set 202*a*, 202*b* in FIG. 2A, it is further contemplated that a set may include other quantities of actuator links 203. For example, one or each of sets 202*a*, 202*b* may comprise four or more actuator links 203. In examples where a set includes more than three actuator links 203, a radial spacing between each actuator link 203 may be less than about 120°. Furthermore, although the actuator links 203 are described above as being coupled to the coupling rings 204, the actuator links 203 may be directly coupled to the tool shaft 218 or the surgical tool 140 via spherical joints without the utilization of a coupling ring.

In certain embodiments, proximal ends 214 of the actuator links 203 attach to a support frame 206 disposed radially outward of the tool shaft 218 and/or surgical tool 140. The proximal ends 214 couple to the support frame at attachment points located on different horizontal planes from the attachment points of the distal ends 212 with the coupling rings 204 or tool shaft 218 and/or surgical tool 140. Accordingly, the actuator links 203 may be described as being vertically angled (e.g., non-parallel with horizontal planes $X_1$ and $X_2$ or vertical axis Y of the slave apparatus 120). The support frame 206 may include any suitable structure to support the quantity of actuator links 203 utilized for the slave apparatus 120. In the embodiment of FIG. 2A, the support frame 206 includes two ring-like bases 208 and three support columns 209 extending therebetween, which may be parallel to the vertical axis Y of the slave apparatus 120. Note that although two bases 208 and three support columns 209 are described, the slave apparatus 120 may include more or less bases and columns having any desired morphologies. The support columns 209 and/or bases 208 act as anchoring points for the actuator links 203, which may be coupled to the support columns 209 and/or bases 208 by any suitable type of spherical joints 215 enabling at least 3-DOF rotational movement. For example, the spherical joints 215 may have a ball-and-socket design, similar to that of the human hip joint, allowing free rotation of the actuator links 203 in two planes, while also preventing translation in any direction. In another example, the spherical joints 215 are gimbal-type spherical joints.

Similarly, the distal ends 212 of the actuator links 203 may also be coupled to the coupling rings 204, tool shaft 218, or surgical tool 140 by a spherical joint 216. The utilization of two spherical joints 215, 216 at opposing ends of the actuator links 203 enables movement of the surgical tool 140 in all three planes. Thus, the actuator links 203 may provide x, y, and z transitional movement as well as pitch and yaw rotational movement for the surgical tool 140, enabling up to 6-DOF of mobility for the surgical tool 140 (and up to 7-DOF when utilized with a rotary actuator coupled to the surgical tool 140, described below).

In some embodiments, the slave apparatus 120 further includes a rotary actuator to provide 360° rotational movement of the tool shaft 218 and/or the surgical tool 140, thus enabling redundant 7-DOF tool roll of the surgical tool 140. In certain embodiments, the rotary actuator is coupled to or disposed within one of the one or more coupling rings 204 or the tool shaft 218, and thus may directly rotate the surgical tool 140. In other embodiments, the rotary actuator is coupled to the ring-like bases 208, enabling rotation of the support columns 209 and ultimately, the surgical tool 140. The rotary actuator may include any suitable type of rotary mechanism, including a zero-backlash piston driven rack and pinion, a single or dual rotary vane actuator, and the like. In some embodiments, the slave apparatus 120 also optionally includes a torque transducer or torque sensor coupled to or disposed within the coupling rings 204 and/or the tool shaft 218 for torque feedback.

The actuator links 203 of the slave apparatus 120 utilize a direct drive system with commutated linear motors 222 having electromagnetic brakes to manipulate the surgical tool 140. Utilization of commutated linear motors over more conventional motors may eliminate mechanical components that can introduce backlash or compliance and degrade positioning accuracy and repeatability, while also reducing load inertia and enabling more dynamic moves with less overshoot and oscillation. Further, commutated slotless linear motors facilitate smooth force control and high fidelity force feedback by enabling passive backdriving.

In certain embodiments, the motors 222 include 3-phase slotless brushless moving magnet linear motors with digital sine wave commutation and optional air bearings. For example, in certain embodiments, the motors 222 include slotless brushless direct current (DC) (BLDC) linear motors.

In such embodiments, the motors 222 may utilize a neodymium iron boron (NdFeB) magnet as a permanent magnet. Each motor 222 may be used in combination with a relative linear encoder (e.g., an optical or holographic linear encoder) for both commutation and control, and/or absolute linear encoders to remove the need for homing. The utilization of slotless brushless moving magnet linear motors provides several advantages over other types of motors (e.g., slotted motors), such as extremely small cogging torque (e.g., torque ripple). Thus, slotless brushless moving magnet linear motors enable more accurate driving with reduced vibration and noise during use thereof. Furthermore, the utilization of air bearings facilitates frictionless high-precision positioning with smooth, controlled velocity and high guiding accuracy. Together with the actuator links 203, the motors 222 form a direct drive system that enables the robotic surgical system 100 to better perform force control, since geared and hydraulic drive systems may suffer from the effects of static and dynamic friction and/or backlash.

Note that, in certain embodiments, slotless brushless moving magnet linear motors, substantially similar to those of the slave apparatus 120, may also be utilized for the master apparatus 110. Furthermore, the rotary actuator of the slave apparatus 120 may include a slotless BLDC-type moving magnet (NdFeB) motor to drive tool roll axis for the surgical tool 140.

As described above, the slave apparatus 120 is configured to indirectly mount to the head of a patient 102. Thus, in order to alleviate pressure on the patient's head created by the weight of the slave apparatus 120 and, in particular, the drive motors 222, one or more components of the slave apparatus 120 may be formed of lightweight high modulus/density ratio materials. For example, in certain embodiments, the bases 208, support columns 209, coupling rings 204, and/or tool shaft 218 are formed of fiber reinforced engineering plastics, aluminum, Kevlar, carbon fiber, or the like in order to reduce weight applied to the patient's head by the robotic surgical system 100. In addition to utilizing lightweight materials for the slave apparatus 120, a counterbalancing support arm, such as articulating arm 160, may be utilized to support the slave apparatus 120, described in more detail below.

Figure 2B:
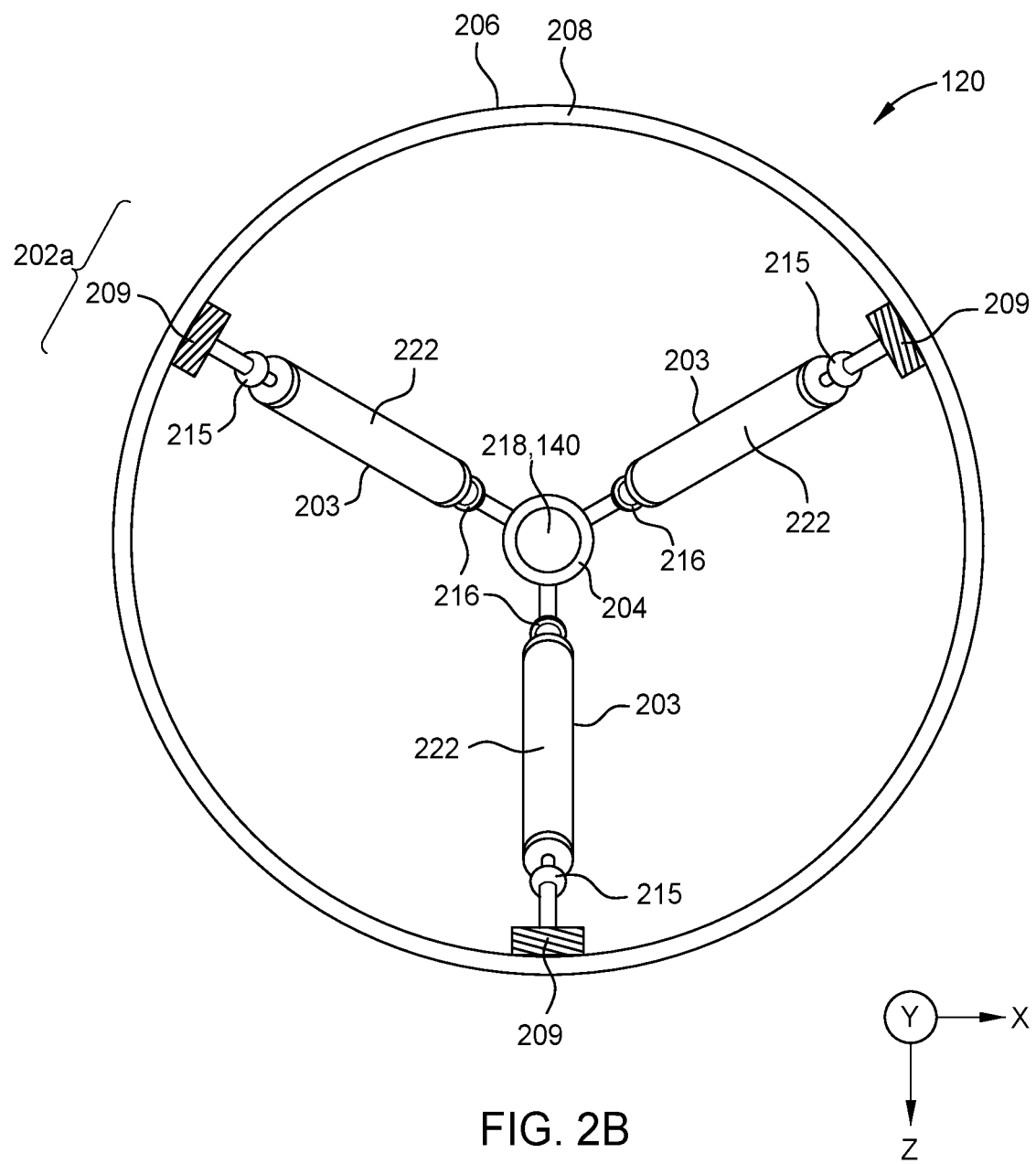
FIG. 2B illustrates an example schematic top-down view of the slave apparatus of FIG. 2A, according to certain embodiments of the present disclosure.

FIG. 2B illustrates a schematic top-down view of the dual tripod slave apparatus 120 of FIG. 2A. The slave apparatus 120 includes two sets 202a, 202b of three actuator links 203, wherein each actuator link 203 is radially spaced apart from an adjacent actuator link 203 of the same set by an angle of about 120°. Furthermore, each actuator link 203 is horizontally or radially aligned (e.g., disposed directly above or below along the axis Y when in a neutral position) with an actuator link 203 of an adjacent set 202 disposed above or below in relation thereto. Thus, only one set 202a of actuator links 203 is visible in the foreground of FIG. 2B, and only three support columns 209 are utilized for anchoring the actuator links 203 to the support frame 206. Accordingly, the arrangement of the actuator links 203 depicted in FIGS. 2A and 2B may be described as "aligned".

Figure 2C:
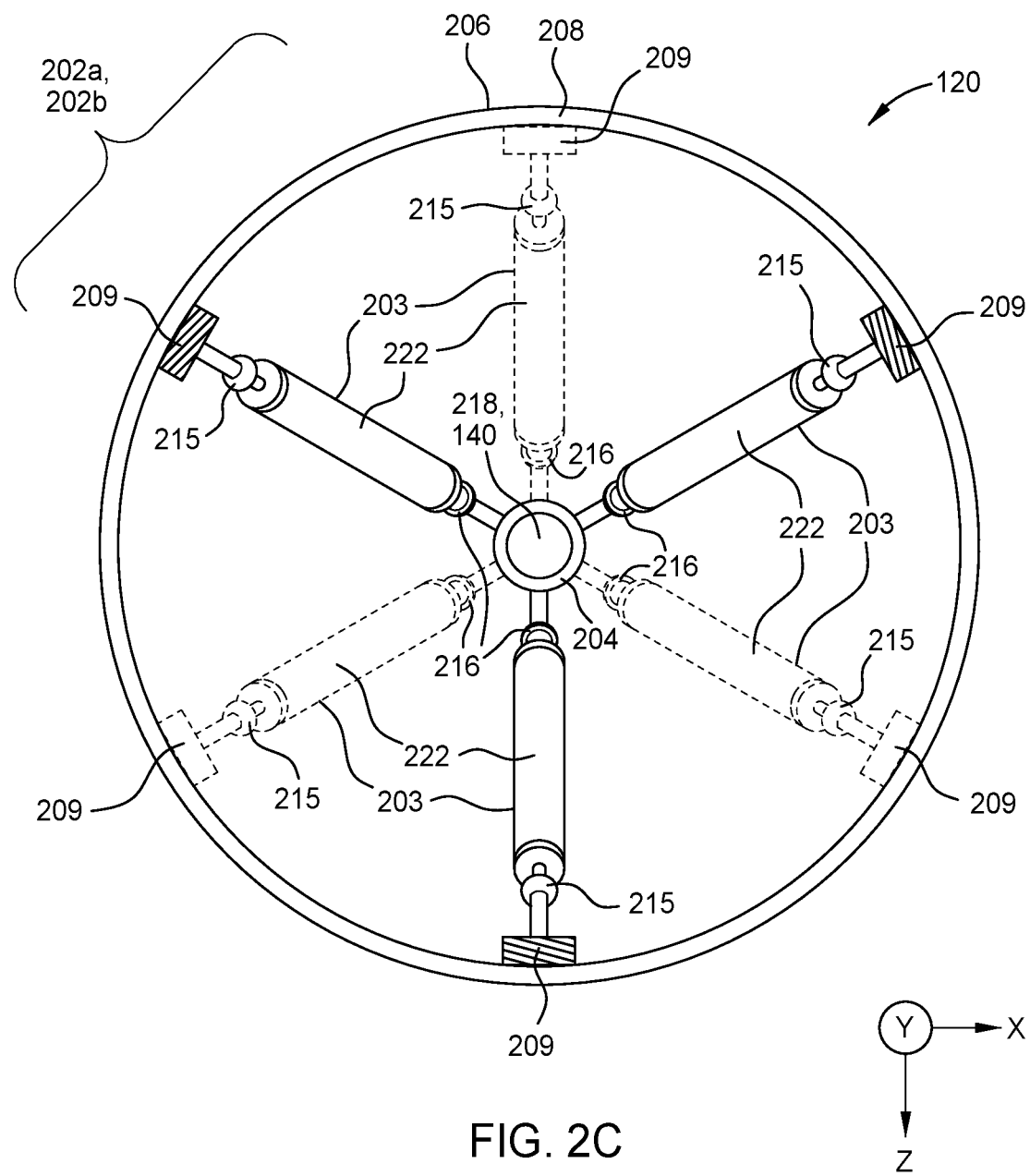
FIG. 2C illustrates an example schematic top-down view of the slave apparatus of FIG. 2A, according to certain embodiments of the present disclosure.

FIG. 2C illustrates a schematic top-down view of the dual tripod slave apparatus 120 wherein the actuator links 203 are horizontally or radially offset (e.g., unaligned along the axis Y) between adjacent sets 202. As shown, the slave apparatus 120 still maintains a dual tripod structure having two sets 202a, 202b of three actuator links 203 radially spaced apart at an angle of about 120°. However, unlike the embodiments of FIGS. 2A and 2B, each actuator link 203 is unaligned with the actuator link 203 of the adjacent set 202 disposed above or below in relation thereto. Thus, both sets 202a, 202b of actuator links 203 are visible in FIG. 2C (one set 202b is depicted in phantom), and six support columns 209 are utilized to support both sets 202 of actuator links 203. The utilization of this horizontally or radially offset arrangement of the actuator links 203 may enable a different degree of mobility (e.g., range of articulation) for the surgical tool 140 as compared to the aligned structure described above, and thus, may be preferred in some instances.

Figure 3:
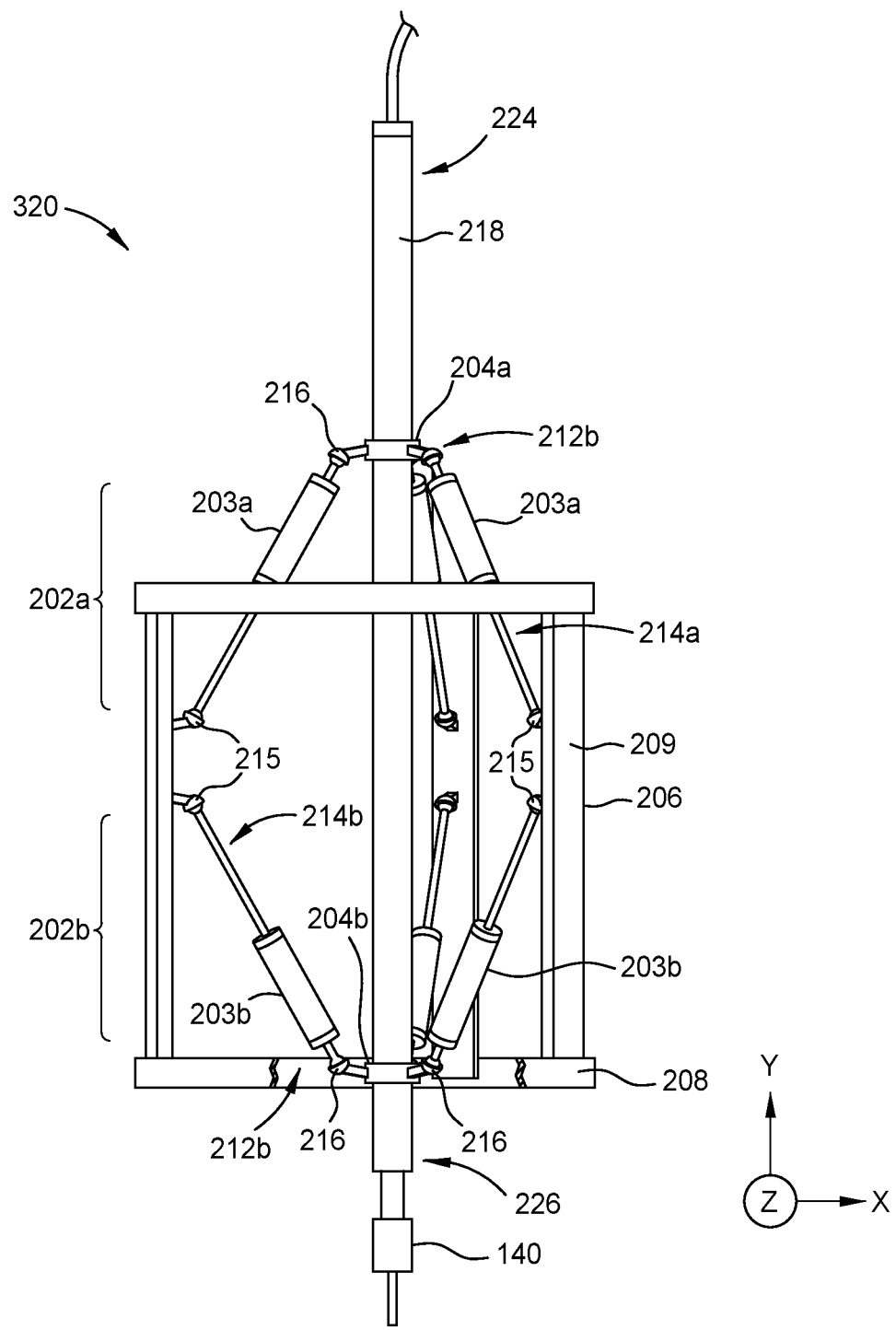
FIG. 3 illustrates a perspective view of another example slave apparatus configured to be utilized with the robotic surgical system of FIG. 1, according to certain embodiments of the present disclosure.

FIG. 3 illustrates a perspective view of an alternative slave apparatus 320 of the robotic surgical system 100, according to certain embodiments. As depicted in FIG. 3, the relationships of the vertical positions of the distal ends 212 and the proximal ends 214 of the actuator links 203 (e.g., the vertical orientations or angles of the actuator links 203) between each set 202a, 202b are inverted. That is, in one set 202a, the distal ends 212a of the actuator links 203a are coupled to the tool shaft 218 or surgical tool 140 at the coupling ring 204a, which is disposed at a position along a length of the tool shaft 218 or surgical tool 140 located above the coupling point of the proximal ends 214a with the support columns 209 in relation to the vertical axis Y. Conversely, the distal ends 212b of the actuator links 203b in set 202b are coupled to the tool shaft 218 or surgical tool 140 at the coupling ring 204b disposed at a position located below the coupling point of the proximal ends 214b with the support columns 209 in relation to the vertical axis Y. This alternative embodiment differs from those described with reference to FIGS. 2A-2C, wherein both sets of actuator links 202a, 202b have substantially similar vertical orientations and/or angles.

Figure 4:
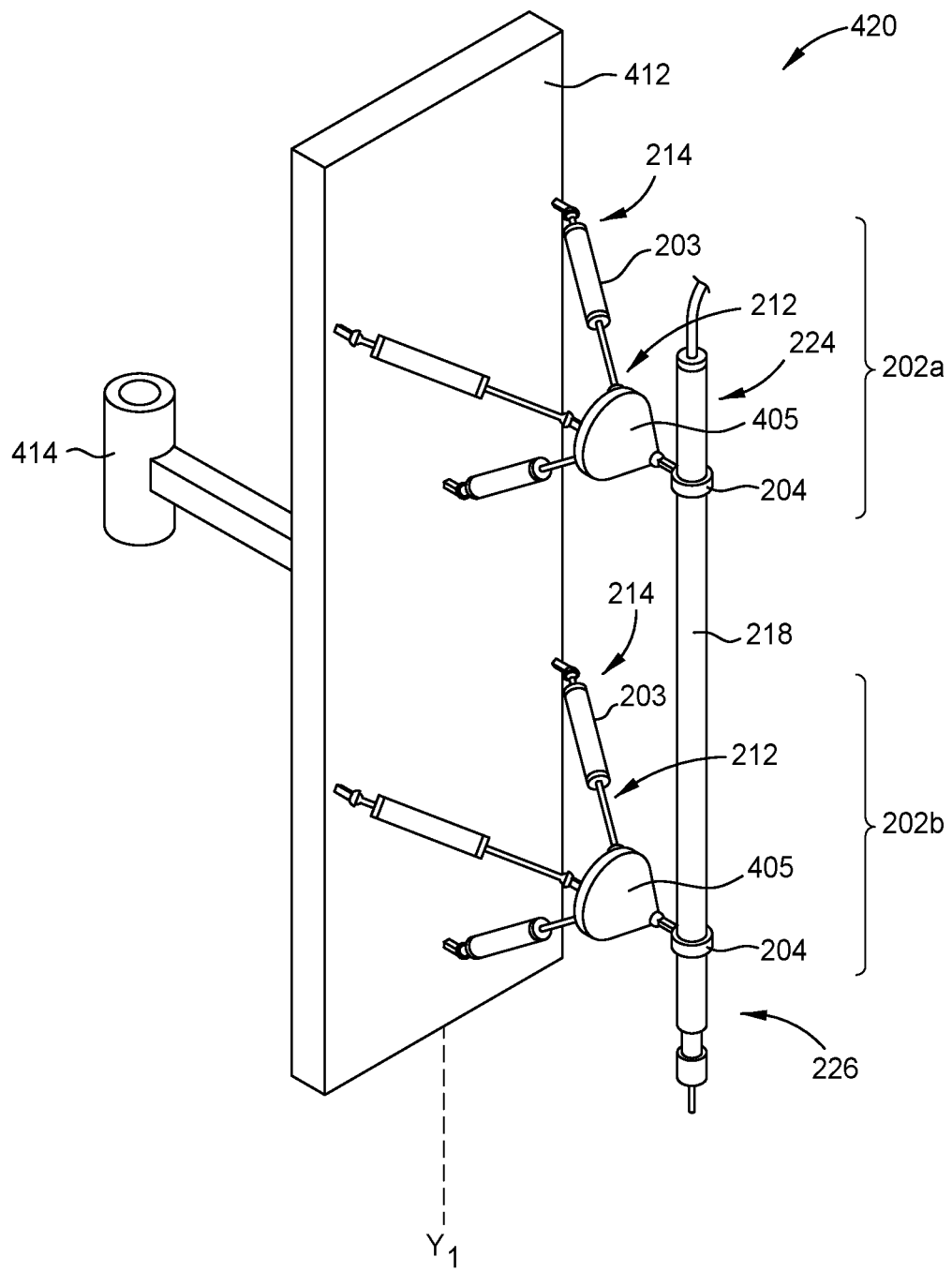
FIG. 4 illustrates a perspective view of another example slave apparatus configured to be utilized with the robotic surgical system of FIG. 1, according to certain embodiments of the present disclosure.

FIG. 4 illustrates a perspective view of yet another alternative slave apparatus 420 of the robotic surgical system 100 according to certain embodiments. Similar to the slave apparatus 120 and 320, the slave apparatus 420 includes two sets 202a, 202b of three actuator links 203, each indirectly coupled to the tool shaft 218 or the surgical tool 140 near the distal ends 212 thereof. However, unlike the embodiments described above, the two sets 202a, 202b of actuator links 203 are further coupled directly or indirectly to a single actuation platform 412 at the proximal ends 214 thereof such that the proximal ends 214 are aligned along a single vertical plane $Y_1$. The actuation platform 412 acts in a manner similar to the support columns 209 and provides mounting support for the actuator links 203. In certain embodiments, the actuation platform 412 includes a rotational joint 414 (e.g., a hinge enabling horizontal and/or vertical rotation) on a backside thereof for rotatable coupling with an extension of the forehead support 150, described in greater detail with reference to FIGS. 5A and 5B.

In certain embodiments, the distal ends 212 of the actuator links 203 in each set 202a, 202b are connected to the coupling rings 204 and/or tool shaft 218 and/or surgical tool 140 via an intermediary platform 405 upon which the distal ends in each set 302a, 302b converge. The intermediary platforms 405 enable the translation of linear movement from actuator links 203 into corresponding transitional and rotational manipulation of the surgical tool 140. Accordingly, both sets 202a, 202b of actuator links 203 may act in concert to provide x, y, and z transitional movement, as well as pitch and yaw rotational movement. In combination with the utilization of a rotary actuator that may be coupled to the coupling rings 204 and/or tool shaft 218, the actuator links 203 enable up to 7-DOF of the tool shaft 218 and/or tool 140. Note that although the intermediary platforms 405 are depicted as having a conical shape, the intermediary platforms 405 may have any suitable morphology to enable translation of the linear movement of the actuator links 403 into up to 6-DOF movement of the surgical tool 140.

Although the structures depicted in FIGS. 2A-2C, 3, and 4 are described with reference to the slave apparatus 120, the same or substantially the same structures and arrangements may be utilized for the master apparatus 110. For example, when utilizing the dual tripod slave apparatus 120, the master apparatus 110 may mimic the slave apparatus 120 and share the same dual tripod structure, though scaled up for easier manipulation by the operator 106. Accordingly, the master apparatus 110 may include a master surgical tool handle replicating the surgical tool 140 and coupled to two sets of three radially extending master actuator links, wherein each set of the master actuator links is coupled to the master surgical tool handle along a single horizontal plane to form a dual tripod structure. Further, the master apparatus 110 may include slotless BLDC-type master motors, which facilitate torque feedback when used in combination with torque sensors.

By mimicking the mechanical structure of the slave apparatus 120 for the master apparatus 110, complete general spatial motion of the slave apparatus 120 and thus, the surgical tool 140, is enabled. Furthermore, mimicking of the mechanical structure of the slave apparatus 120 for the master apparatus 110 may improve ease of use for the operator 106, as the positions for the slave apparatus 120 and the master apparatus 110 may be made identical but for structure scaling. A dual tripod structure for the master apparatus 110 also enables the operator 106 to perform surgical procedures with the robotic surgical system 100 utilizing only one hand and thus, the operator 106 may simultaneously use his or her other hand for other actions such as for positioning of an endoilluminator or a second tool. In some embodiments, a pair of robotic surgical systems 100 may be utilized in combination to perform two-handed surgery by the operator 106, each hand of the operator 106 controlling an individual robotic surgical system 100 and thus, an individual slave apparatus 120.

Figure 5A:
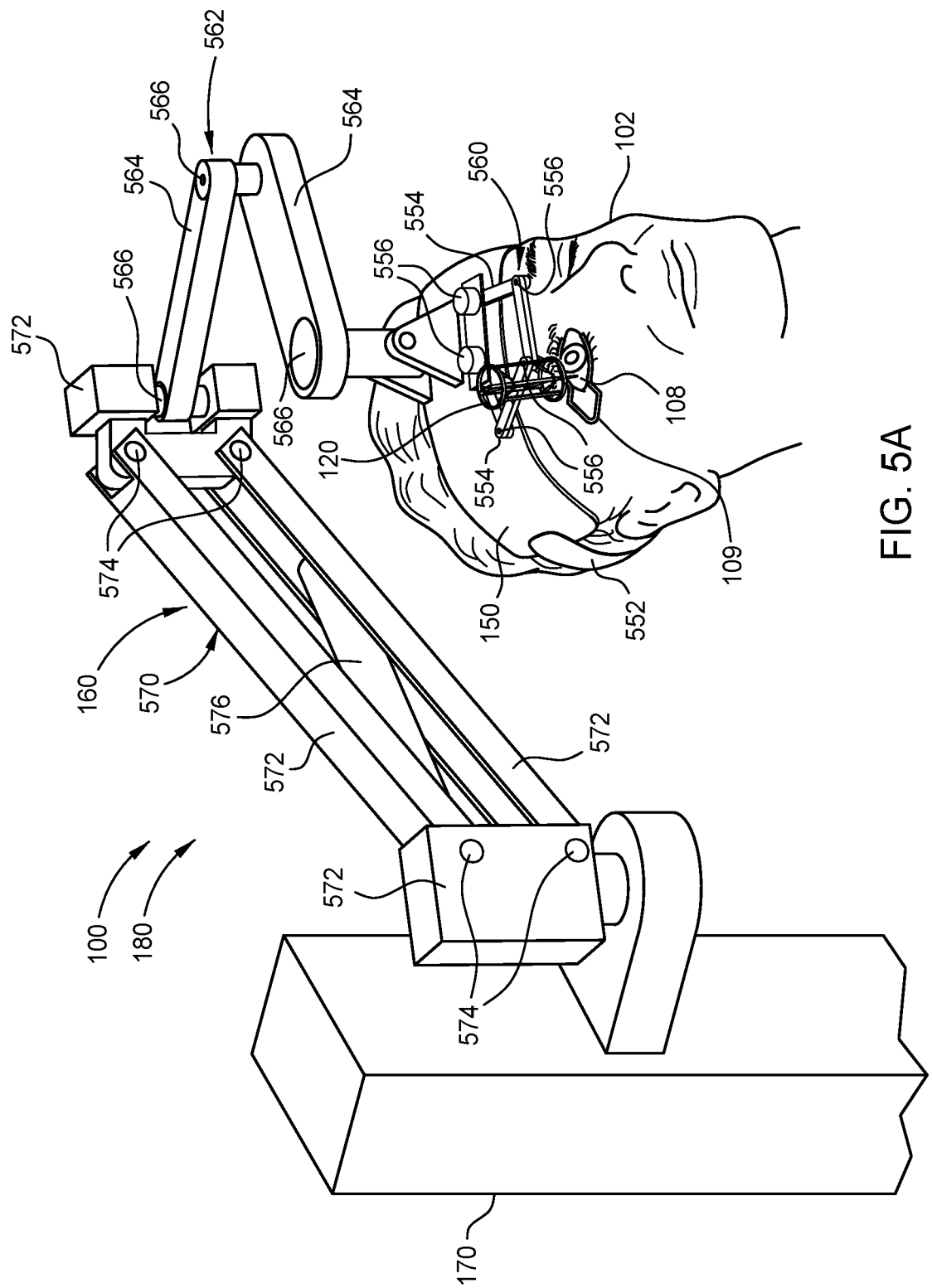
FIG. 5A illustrates a perspective view of an example slave apparatus mounted to a patient's head, according to certain embodiments of the present disclosure.
Figure 5B:
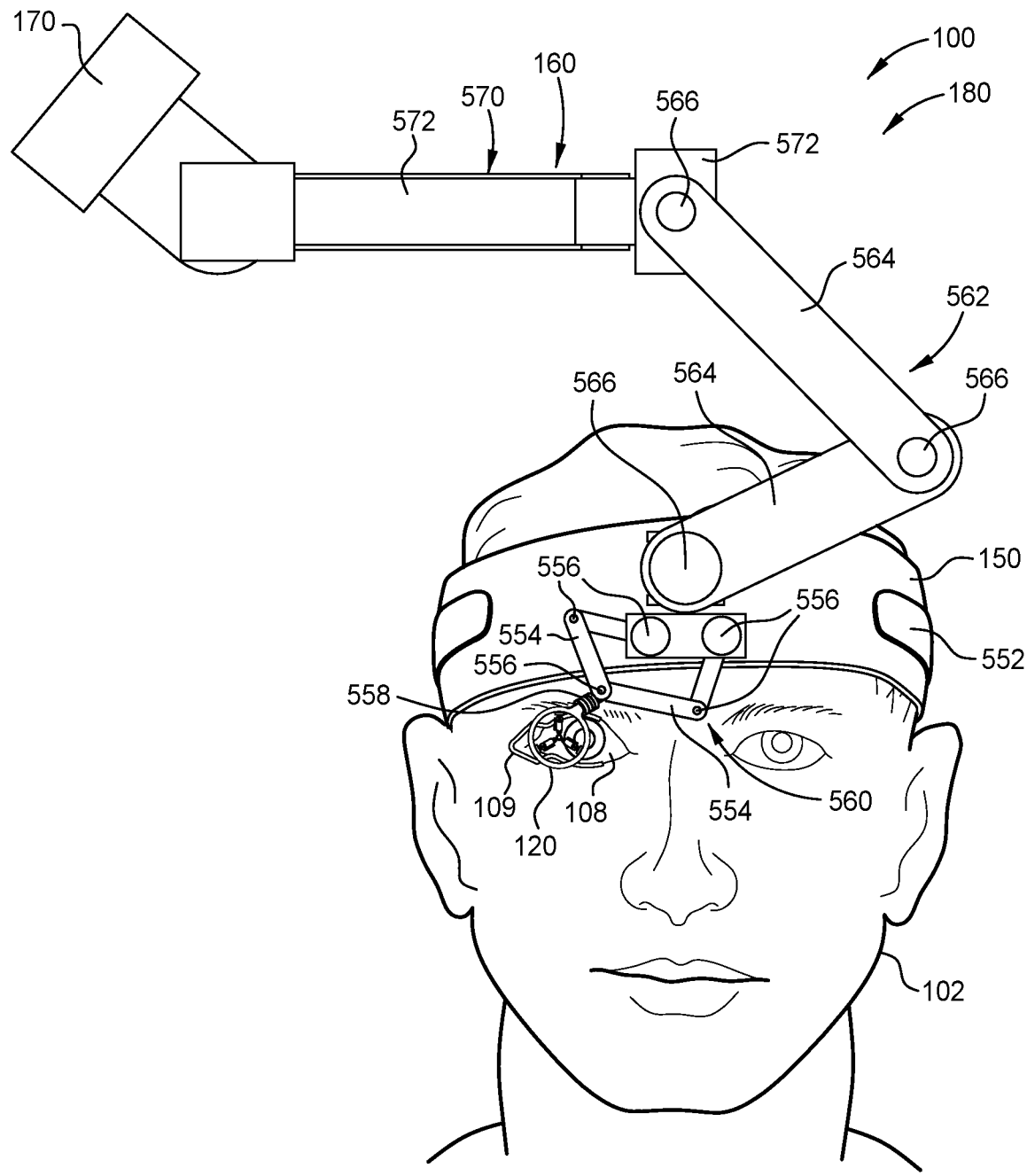
FIG. 5B illustrates a perspective view of an example slave apparatus mounted to a patient's head, according to certain embodiments of the present disclosure.

FIGS. 5A and 5B illustrate perspective views of the slave apparatus 120 when mounted to the head of the patient 102, according to certain embodiments. Accordingly, FIGS. 5A and 5B are herein described together for clarity. As shown, the slave apparatus 120 is coupled to the slave apparatus support system 180. In certain aspects, the slave apparatus support system 180 aids in supporting the slave apparatus 120 in an upright and secured (e.g., fixed) position over the patient's eye 108, which is held open by a speculum 109, to prevent relative movement between the patient's head and the slave apparatus 120. For example, when the slave apparatus 120 is attached to the slave apparatus support system 180 and mounted on the patient's head, the slave apparatus 120 will move with the patient's head, thereby eliminating, or at least reducing, the need for general anesthesia and neuromuscular blockade. Anesthesia and neuromuscular blockades are typically used to prevent patient movement during surgical procedures, which can disrupt utilization of the surgical tool 140 and/or lead to surgical instrument-induced damage of the patient's eye. Thus, the risks associated with involuntary movement of the patient may be greatly reduced or eliminated by utilizing the slave apparatus 120 and slave apparatus support system 180. In certain aspects, the slave apparatus support system 180 further reduces or eliminates any pressure against the patient's head caused by the weight of the slave apparatus 120 by employing a counterbalancing mechanism. Accordingly, the patient 102 will not feel the weight of the slave apparatus 120, but may still feel the inertia, which will slow down and discourage patient movement.

The slave apparatus support system 180 generally includes the forehead support 150, articulating arm 160, and base 170. The forehead support 150 is a sterilizable or disposable U-shaped support configured to contact and rest on the patient's forehead and temples. In order to improve comfort for the patent 102, an underside or patient-facing side of the forehead support 150 includes a surface padded with, for example, a viscoelastic material, such as dense memory foam. In certain embodiments, the forehead support 150 is secured to the patient's head utilizing a broad and adjustable head strap 552, which may be fastened via any suitable fastening mechanism. In certain embodiments, the head strap 552 is adjustably fastened via a hook and loop fastener such as, for example, Velcro®, to enable a customized fit with respect to the patient. By attaching the slave apparatus 120 to the patient's head via the forehead support 150, patient head rotation relative to the slave apparatus 120 is virtually eliminated.

The slave apparatus 120 is attached to the forehead support 150 via an adjustable attachment 560 to accommodate different patient anatomical characteristics (e.g., head geometries) and enable lateral positioning of the slave apparatus 120 over the desired patient's eye 108. In certain embodiments, the attachment 560 includes an articulating arm, such as a single serial articulating arm or two parallel articulating arms, medially attached to the forehead support 150 to facilitate positioning of the slave apparatus 120 over either of the patient's eyes. In the embodiment of FIGS. 5A and 5B, the attachment 560 is shown as having two parallel articulating arms 554 with two linkages each, and five revolute joints 556, which the linkages rotate about laterally. In certain embodiments, the attachment 560 further includes a distal revolute joint 558 at a distal end thereof to enable rotation of the slave apparatus 120 about a horizontal axis.

In order to support the weight of the slave apparatus 120, the forehead support 150 is further coupled to the counterbalancing and passive articulating arm 160 supported by the base 170. In certain embodiments, the articulating arm 160 includes a SCARA mechanism 562 to allow passive, lockable horizontal movement of the forehead support 150 and the slave apparatus 120 attached thereto, as well as a four-bar parallelogram mechanism 570 to enable passive, lockable vertical movement thereof. For example, as shown in FIGS. 5A and 5B, the SCARA mechanism 562 is formed by at least two links 564 and at least three revolute joints 566 having vertical axes to create passive motion parallel to a floor plane of the operating room. The four-bar parallelogram mechanism 570 is formed by four bars 572 and four revolute joints 574 having horizontal axes to create passive vertical motion perpendicular to the floor plane. The four-bar parallelogram mechanism 570 is further counterbalanced by a spring 576, such as an air spring, constant force spring, or the like, which enables locking of the four-bar parallelogram mechanism 570. Together, the SCARA mechanism 562 and the four-bar parallelogram mechanism 570 provide an adjustable counterbalancing mechanism to account for the weight of the slave apparatus 120, which is mounted to and moves with the patient's head during a surgical procedure for increased patient safety in the context of patient head movement. Note that although the passive articulating arm 160 is shown as having the SCARA mechanism 562 at a distal end thereof and the four-bar parallelogram mechanism 570 at a proximal end thereof, the passive articulating arm 160 may include the two mechanisms in any order or arrangement as desired.

Figure 6:
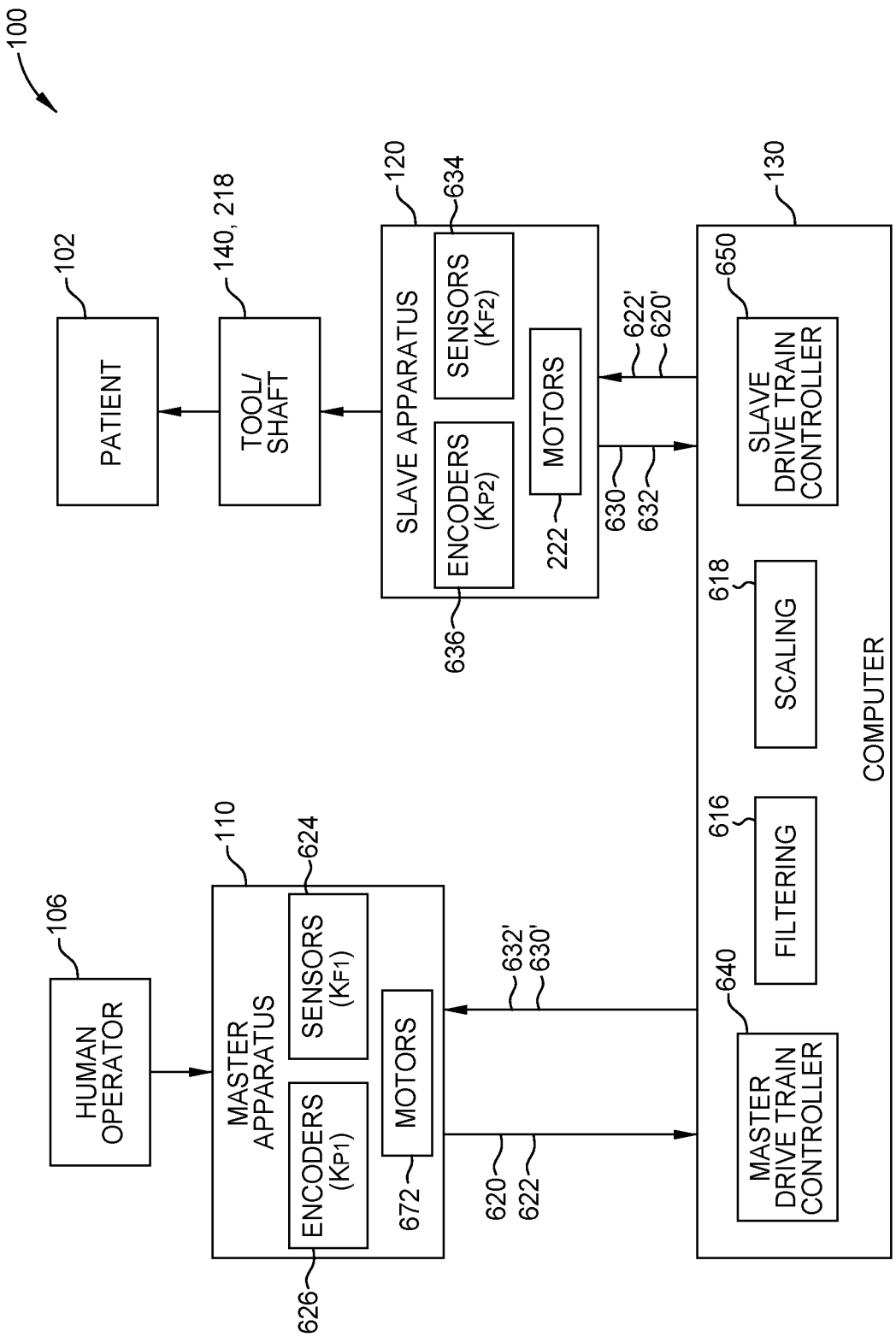
FIG. 6 illustrates a block diagram of the robotic surgical system of FIG. 1, according to certain embodiments of the present disclosure.

FIG. 6 illustrates a block diagram of a signal flow of the robotic surgical system 100. As described above, the robotic surgical system 100 employs a master-slave type system that includes the master apparatus 110 and the slave apparatus 120, which may have substantially similar architectures or arrangements with one another. When the operator 106 operates the master apparatus 110, the master apparatus 110 generates a control signal that is transmitted between the master apparatus 110, the computer 130, and the slave apparatus 120. Receiving the control signal, the slave apparatus 120 controls the operation of a surgical tool 140.

The master apparatus 110 includes a plurality of master encoders 626 and master force sensors 624 communicatively coupled therewith and configured to provide 6-DOF force and tactile feedback to the operator 106 during use. In certain embodiments, the master encoders 626 include a rotary encoder communicatively coupled to a master surgical tool handle to sense angular position and/or a torque sensor to sense static and/or dynamic torque applied thereto. In embodiments wherein the master apparatus 110 includes a dual tripod architecture similar to the slave apparatus 120, each master actuator link may be in communication with one or more master encoders 626 and/or one or more master force sensors 624. For example, each master actuator link may correspond to one master encoder 626 and one master force sensor 624. However, any suitable number of master encoders 626 and master force sensors 624 may be utilized depending on the structure of the master apparatus 110. In certain embodiments, the number of the master actuator links, master encoders 626, and master force sensors 624 depends upon the number of actuator links 203 of the slave apparatus 120. For example, the master apparatus 110 may comprise at least one master actuator link, master encoder 626, and master force sensor 624 per actuator link 203 of the slave apparatus 120, such as six master actuator links, six master encoders 626, and six master force sensors 624 when the slave apparatus 120 comprises six actuator links 203. In another example, the master apparatus 110 includes an additional seventh master encoder 626 and seventh master force sensor 624 in communication with the master surgical tool handle.

In certain embodiments, the master encoders 626 include fiber-optic-coupled sine-cosine (i.e., sine) encoders providing position and direction values of the master as analog sine waves. In certain embodiments, the master encoders 626 include linear optical encoders, such as linear optical absolute encoders and linear optical incremental encoders. In certain embodiments, the master force sensors 624 include strain gauges.

As the operator 106 manipulates the master apparatus 110, the movement thereof drives a plurality of master motors 672 (e.g., slotless BLDC-type motors), causing one or more of the master encoders 626 to read different positions ($K_{P1}$) of one or more master actuator links. Simultaneously, one or more master force sensors 624 sense the movement of the master actuator links as they impart forces ($K_{F1}$) on the structure of the master apparatus 110. The master force sensors 624 and the master encoders 626 act to send a plurality of values (e.g., signals) 622 corresponding with the $K_{P1}$ and a plurality of values 620 corresponding with the $K_{F1}$ to the computer 130, which then reads the values 620, 622 and applies various filtering 616 and scaling 618 (e.g., gain, reduction, compensation, adjustment) to the values. Thereafter, the computer 130 sends an updated control signal comprising filtered and scaled values 620', 622' to the slave apparatus 120 via a slave drive train controller 650. The signals instruct the motors 222 to linearly actuate the actuator links 203 and/or rotate the rotary actuator coupled directly or indirectly to the surgical tool 140 and/or the tool shaft 218. Accordingly, the slave apparatus 120 is manipulated in a desired movement or to a desired position to perform surgical maneuvers with the surgical tool 140 on the patient 102.

The slave apparatus 120 optionally has a set of slave encoders 636 and slave force sensors 634. For example, the slave apparatus 120 includes a set of six or seven slave encoders 636 and six or seven slave force sensors 634, each slave encoder 636 and/or slave force sensor 634 corresponding with a single actuator link 203 and/or the surgical tool 140. In certain embodiments, the slave encoders 636 are substantially similar to the master encoders 626, and may include fiber-optic-coupled sine-cosine (i.e., sine) encoders and/or linear optical encoders. Similarly, the slave force sensors 634 may be substantially similar to the master force sensors 624 and include strain gauges. In certain examples, the slave apparatus 120 include strain gauges 634 coupled to the surgical tool 140 and/or the actuator links 203 that are configured to sense contact forces at the 30-320 Hz (Hertz) domain, otherwise known as the fidelity channel. In certain embodiments, the slave apparatus 120 optionally includes a torque transducer or torque sensor configured to sense static and/or dynamic torque applied to the surgical tool 140. In further embodiments, the slave apparatus 120 includes a single force-sensing device configured to provide 6-DOF force feedback for the entire slave apparatus 120.

As the slave apparatus 120 is commanded to manipulate the surgical tool 140, the slave encoders 636 read different positions ($K_{P2}$) of the actuator links 203 and the slave force sensors 634 simultaneously sense contact and torque forces ($K_{F2}$) against the surgical tool 140. A plurality of values 632 corresponding with the $K_{P2}$ and a plurality of values 630 corresponding with the $K_{F2}$ are then sent back to the computer 130, which applies filtering 616 and scaling 618 and translates the updated control signal comprising filtered and scaled values 620', 622' to the master apparatus 110 via a master drive train controller 640. Generally, the values 632, 630 are up-scaled by the computer 130 for translation to the master apparatus 110, while the values 622, 620 are down-scaled for translation to the slave apparatus 120. In certain embodiments, the values 622, 620 and 632, 630 are scaled according to fixed scaling factors. In other embodiments, the values 622, 620 and 632, 630 are scaled according to dynamic scaling factors.

The master motors for the master apparatus 110 are then driven by the scaled signals and the operator 106 can sense contact with different types of surfaces and/or tissues during ophthalmic surgery, such as vitreoretinal surgery. In addition to translating signals between the master apparatus 110 and the slave apparatus 120, the computer 130 coordinates the actuator links of each of the master apparatus 110 and the slave apparatus 120. Kinematic and dynamic models are loaded into the computer 130 to stabilize the system and provide coordinated 6-DOF or 7-DOF motion to the slave apparatus 120 coupled to the surgical tool 140. In certain embodiments, the robotic surgical system 100 includes one or more electromagnetic brakes for each robot axis. For example, braking of the robotic surgical system 100 may be controlled in part by watchdog timers, a power failure sensor, and/or differences determined by the computer 130 between control signals (i.e., commanded position and pose, upon filtering 616 and scaling 618) versus encoder-sensed actual position and pose.

The execution of filtering 616 and scaling 618 of values by the computer 130 during transmission of values between the slave apparatus 120 and the master apparatus 110 provides numerous benefits during operation of the robotic surgical system 100. Accordingly, many of the disadvantages that may be associated with manual surgery, as well as conventional robotic surgical systems, may also be averted. For example, involuntary operator movement or operator tremor (i.e., physiological tremor), which is very common with inexperienced or low volume surgeons as well as some older surgeons, may be filtered by a tremor filter of the computer 130. Physiological tremor leads to an intolerable imprecision of surgical procedures that require a positioning accuracy of about 10 µm (micrometers) and below. Typically, physiological hand tremor lies in the band of 8-15 Hz with an amplitude of 50 µm and can be approximated by a sinusoidal movement, whereas controlled hand movement of a surgeon during microsurgeries (e.g., vitreoretinal surgery) is usually less than 1 Hz. For effective tremor filtering, the robotic surgical system 100 may utilize one or more adaptive algorithms loaded into the computer 130 to create zero-phase lag in the filtering process to filter tremor from the master output in real-time. In certain embodiments, filtering 616 is executed by a zero-phase delay low-pass filter (LPF) with a cut-off frequency of 5 Hz. For example, the filter may be a first-order Butterworth LPF.

As described above, the computer 130 is further configured to execute force downscaling, force limiting, position scaling, and velocity scaling between the master apparatus 110 and the surgical tool 140 during the scaling operations 618. Force downscaling, force limiting, and position and velocity scaling may together be described as the user interface control law embedded within the robotic surgical system 100. As illustrated in FIG. 6, the robotic surgical system 100 may utilize a closed control loop to control force and positioning of the slave apparatus 120. The closed control loop may further be utilized to provide haptic feedback to the operator 106 during use thereof. For example, the master force sensors 624 may sense operator forces upon the master apparatus 110, which may then be converted into downscaled control signals provided to the slave apparatus 120. The sensed force values may be scaled by utilizing a software and user interface controllable scaling ratio or a fixed or predetermined scaling ratio loaded into the computer 130. In some examples, the computer 130 may be configured to execute cooperative control algorithms to generate movement of the slave apparatus 120 based on a scaled difference between tool-tissue and operator forces.

In addition to force control, the robotic surgical system 100 provides force or tactile (e.g., haptic) feedback between the surgical tool 140 and the master apparatus 110. In certain embodiments, the robotic surgical system 100 includes a haptic feedback system (e.g., feedback loop) separate from the closed control loop described above. In other embodiments, the haptic feedback loop is integrated with the force and positioning control loop. Generally, the haptic feedback loop collects and transmits tactile information between the surgical tool 140 and the master apparatus 110 in a domain of between about 30 Hz and up to about 320 Hz in order to enable the operator 106 to distinguish biomechanical properties of tissues during surgery.

In summary, embodiments of the present disclosure include devices and systems for improving the accuracy and dexterity of ophthalmic surgical operations while minimizing trauma to the patient. Voluntary and involuntary patient movement during surgical procedures, and in particular, delicate and precise procedures such as vitreoretinal surgery, may typically cause undesired and accidental contact between surgical tools and ocular tissues. Such contact may lead to serious complications to the patient's eye, which can develop into potentially irreversible damage and visual impairment. The devices and systems described herein include embodiments wherein a surgeon may mount and secure a surgical slave apparatus to the head of a patient such that the slave apparatus moves along with the head of a patient during use thereof. By utilizing the devices and systems described herein, many of the risks associated with patient movement during ophthalmic surgical procedures may be reduced or eliminated. Accordingly, the described embodiments also eliminate, or at least reduce, the need for the provision of general anesthetics with neuromuscular blockade, which are utilized in part to prevent patient movement.

Still further, the devices and systems described herein may mitigate some of the inherent restrictions on vitreoretinal surgery related to human sensory and motor limitations. For example, surgeon fatigue, hand tremor, and the inability to perceive miniscule tactile differences between tissues in the ocular space are common limitations on the accuracy and effectiveness of vitreoretinal procedures. By providing mechanisms for force control (e.g., scaling and filtering) and feedback (e.g., tactile feedback) while maintaining 7-DOF movement, the devices and systems described herein provide surgeons with increased dexterity and precision wherein the surgeon has an improved physical connection with the surgical site. Thus, the devices and systems described herein may decrease the risk of surgical error and reduce operative times, thereby increasing the overall effectiveness of vitreoretinal procedures.

Although vitreous surgery is discussed as an example of a surgical procedure that may benefit from the described embodiments, the advantages of the surgical devices and systems described herein may benefit other surgical procedures as well.

While the foregoing is directed to embodiments of the present disclosure, other and further embodiments of the disclosure may be devised without departing from the basic scope thereof, and the scope thereof is determined by the claims that follow.

What is claimed is:

1. A surgical system, comprising:
   a master apparatus;
   a slave apparatus controllably coupled to the master apparatus and configured to be mounted to a patient's head, the slave apparatus comprising:
      a support frame;
      a tool shaft;
      a first set of three or more linearly-actuating links coupled to the support frame, at a proximal end of each link, and to the tool shaft, at a distal end of each link, wherein the first set of links are arranged in a radial manner, each link of the first set radially spaced apart from an adjacent link in the first set by an angle less than or equal to about 120 degrees, wherein the proximal ends of each link of the first set are attached to the support frame such that the proximal ends of each link of the first set cannot translate linearly along the support frame;
      a second set of three or more linearly-actuating links coupled to the support frame, at a proximal end of each link, and to the tool shaft, at a distal end of each link, wherein the second set of links are arranged in a radial manner, each link of the second set radially spaced apart from an adjacent link in the second set by an angle less than or equal to about 120 degrees, wherein the proximal ends of each link of the second set are attached to the support frame such that the proximal ends of each link of the second set cannot translate linearly along the support frame;

a surgical tool coupled to the first and second sets of links through the tool shaft, the first and second sets of links providing translational and rotational movement to the surgical tool through the tool shaft; and one or more direct drive actuators coupled to each link of the first and second sets of links, the direct drive actuators configured to provide linear movement to each link to linearly modify a length of each link between the proximal and distal ends of each link, of the first and second sets of links;

a direct drive rotary actuator coupled to at least the first set of links and the surgical tool, the rotary actuator configured to provide tool axis roll for the surgical tool;

wherein the slave apparatus is further coupled to a slave apparatus support system comprising:
a forehead pad;
an adjustable head strap attached to the forehead pad; and
at least one adjustable arm extending from the forehead pad and configured to support the slave apparatus over an eye of a patient;

wherein the slave apparatus support system further comprises a counterbalancing articulating arm attached to the forehead pad, the counterbalancing articulating arm comprising a SCARA (Selectively Compliant Articulated Robot Arm) mechanism;

wherein the slave apparatus and the master apparatus each comprise at least six force sensors;

wherein the slave apparatus and master apparatus form a closed control loop for force signal values that are detected by the force sensors and translated between the slave apparatus and master apparatus;

wherein the master apparatus comprises a haptic interface configured to receive input from a user to generate one or more control signals for the slave apparatus; and wherein the surgical tool comprises an end effector having a sensor to communicate at least one of force feedback and force control signals to the surgical system.

2. The surgical system of claim 1, wherein the one or more direct drive actuators comprise slotless brushless moving magnet linear motors.

3. The surgical system of claim 2, wherein the one or more direct drive actuators comprise slotless, brushless, linear direct current (DC) motors.

4. The surgical system of claim 1, further comprising a computer configured to limit and scale the force signal values translated between the master apparatus and the slave apparatus.

5. The surgical system of claim 1, wherein the slave apparatus or master apparatus comprise six sine-cosine encoders.

6. The surgical system of claim 5, further comprising a computer configured to scale position signal values that are collected by the encoders and translated between the master apparatus and the slave apparatus.

7. The surgical system of claim 1, wherein the SCARA mechanism is a passive SCARA comprising a passive four-bar parallelogram mechanism counterbalanced by a spring.

8. The surgical system of claim 7, wherein the spring is a constant force spring or an air spring.

9. The surgical system of claim 1, wherein the surgical tool is a device holder configured to secure another device to the slave apparatus and wherein the surgical tool comprises a radio frequency identification (RFID) to communicate with the surgical system.

10. The surgical system of claim 9, wherein the RFID communicates at least one of a tool weight or tool length to the surgical system.

11. The surgical system of claim 1, further comprising at least one of an aspiration or injection connection for the surgical tool.

12. The surgical system of claim 1, further comprising a fiber optic connection for the surgical tool.

* * * * *